United States Patent [19]

Eisenstadt et al.

[11] Patent Number: 5,846,557

[45] Date of Patent: Dec. 8, 1998

[54] CHEWING GUM CONTAINING COUGH SUPPRESSING AGENT

[75] Inventors: Barbara Eisenstadt, Neponsit, N.Y.; Penny A. Cash, Denville; Abraham I. Bakal, Parsippany, both of N.J.

[73] Assignee: Cumberland Packing Corporation, Brooklyn, N.Y.

[21] Appl. No.: 885,382

[22] Filed: Jun. 30, 1997

Related U.S. Application Data

[63] Continuation of Ser. No. 618,950, Mar. 20, 1996, abandoned.

[51] Int. Cl.⁶ ..................................................... A61K 47/00

[52] U.S. Cl. ........................... 424/439; 424/440; 424/441

[58] Field of Search .................................... 424/439, 440, 424/441

[56] References Cited

U.S. PATENT DOCUMENTS

| | | | |
|---|---|---|---|
| 4,929,508 | 5/1990 | Sharma et al. | 424/439 |
| 4,971,798 | 11/1990 | Coia et al. | 424/440 |
| 5,196,436 | 3/1993 | Smith | 514/289 |

*Primary Examiner*—Thurman K. Page
*Assistant Examiner*—D. Faulkner
*Attorney, Agent, or Firm*—Steinberg & Raskin, P.C.

[57] ABSTRACT

The present invention pertains to chewing gum compositions containing cough suppressing agents. The compositions include a taste-masking mixture containing a flavoring agent, an intense sweetening agent and menthol. This combination nullifies the taste or off-note of the cough suppressant. The present invention also pertains to a method preparing the chewing gum composition and methods of treatment which include administering the cough suppressant-containing chewing gum to a patient in need thereof.

21 Claims, No Drawings ived filed Mar. 20, 1996, now abandoned.

CHEWING GUM CONTAINING COUGH SUPPRESSING AGENT

This application is a continuation of application Ser. No. 08/618,950, filed Mar. 20, 1996, now abandoned.

BACKGROUND OF THE INVENTION

The present invention is directed to medicament-containing chewing gum compositions. In particular, the present invention is directed to chewing gum compositions which effectively mask the unpleasant tastes of the medicaments contained therein over extended chewing periods.

People suffering from throat irritation or experiencing coughing commonly take throat lozenges, cough syrups or cough drops for symptomatic relief. Special cases, however, require prescription drugs to control the symptoms. It is commonly accepted that throat irritation and coughing can be reduced by lubrication with sweet and viscous syrups and/or by sustained lubrication with such materials. Thus, for example, cough drops or lozenges often contain sugar and/or honey. Active ingredients can also be interdispersed or incorporated in the sweet vehicles used to prepare the syrups or lozenges. These active ingredients include, for example, dextromethorphan, menthol, peppermint oil and the like.

Over the years, the most widely used dosage forms for dispensing these medicaments have been syrups, hard candy lozenges and chewable candies. Chewing gums have not been successfully used to deliver most active ingredients. It has been shown that it is difficult to extract a sufficient amount of the active ingredient from the chewing gum in the oral cavity during the usual three to five minute chewing period when the flavors and/or sweetener(s) are extracted from the gum.

One of the most popular and effective antitussive agents is dextromethorphan. This medicament however is very bitter and has a highly unacceptable taste. Accordingly, it is usually administered in cough syrups where masking of the bitter taste is relatively easy and the residence time in the oral cavity is relatively brief. Dextromethorphan has also been incorporated into candies. Here again, masking the unpleasant taste is relatively easy because the drug is released together with the candy flavor and the sweeteners. Dextromethorphan has also been included in solid oral dosage forms so that its displeasing organoleptic qualities completely bypass the sense of taste. Attempts to incorporate dextromethorphan in chewing gums, however, have yielded products which are generally unacceptable. Some dextromethorphan-containing chewing gums have been found to have the bitter taste and unacceptable flavor associated with this agent become especially noticeable after the first two to five minutes of chewing. In other chewing gum products, dextromethorphan has been coated in waxes or other materials in order to combat the unpleasant taste. Alternatives to these coating methods have also been sought because the techniques are expensive and time consuming. In short, current techniques have failed to provide acceptable chewing gum products from an organoleptic standpoint.

Menthol is another effective antitussive agent which is commonly used either alone or in combination with other antitussive agents. Therapeutic amounts of menthol, however, have also proven to be difficult to deliver using chewing gums. While some of the menthol is released from currently available gum formulations within the first few minutes of chewing, the remaining portion is trapped in the gum base and is not released. Thus, these products are unacceptable for extended relief of symptoms.

Another problem associated with the incorporation of dextromethorphan or menthol in chewing gums is the release or extraction of the active ingredient from the gum during the usually brief chewing period. The patent literature cites attempts for controlling the release of drugs from chewing gums. For example, U.S. Pat. No. 4,452,821 describes a chewing gum with extended release in which the drug is suspended or entrapped within a wax. U.S. Pat. No. 4,572,832 describes a method for overcoming the unpleasant taste problem by the addition of protein, a polyhydric alcohol and a fatty acid ester to buccal products. This method, however, is not applicable for chewing gums since it is hard to incorporate the protein in the gum matrix. Furthermore, the fatty acid esters soften the gum base to the point that the gum loses its chewing properties. The problems associated with gum softening through the addition of polyalcohols has been recognized in U.S. Pat. No. 4,248,895 which teaches the use of encapsulation with protein. However, this method may not overcome the taste problems associated with the dextromethorphan and/or menthol. Furthermore, the encapsulation technique adds to the costs of the final product.

In view of the foregoing, there are still shortcomings associated with delivering medicaments having an unpleasant taste via chewing gums. The present invention addresses this need.

SUMMARY OF THE INVENTION

It is therefore an object of the present invention to provide an improved chewing gum containing an effective amount of an antitussive agent.

It is a further object of the present invention to provide an antitussive-containing chewing gum composition which effectively masks the taste of the medicament over prolonged periods of chewing.

Another object of the present invention is to provide a method of suppressing coughs and/or soothing throat irritations in patients using chewing gum-based dosage forms.

A further object of the present invention is to provide a method of preparing chewing gum compositions containing taste-masked antitussives.

These and other objects are achieved by the present invention which, in one aspect, includes chewing gum compositions which are capable of delivering an antitussive upon chewing. The chewing gum compositions include an effective amount of an antitussive agent and a sufficient amount of an antitussive taste-masking mixture to mask the taste of the antitussive agent during the time the chewing gum composition is being chewed. The antitussive taste-masking mixture preferably includes a high intensity sweetener, a flavorant and menthol. In preferred aspects on this embodiment, the chewing gum compositions include by weight about 0.0001 to about 5.0% high intensity sweetener, about 0.0001 to about 5.0% flavorant and about 0.001 to about 1.5% menthol.

Preferred antitussive ingredients include dextromethorphan and its related salts, opiate-based cough suppressants, menthol, in addition to that found in the antitussive taste-masking mixture, and related compounds. The antitussive agent is present in amounts ranging from about 0.01 to about 2.5% by weight of the chewing gum composition; with amounts from about 0.1 to 1.0% by weight being preferred; and amounts from about 0.12 to about 0.75% by weight being most preferred. One particularly preferred high intensity sweetener included in the chewing gum compositions is aspartame while preferred flavorants are honey or artificial honey flavors.

In other aspects of the invention there are provided methods of treatment including effecting cough suppression and/or easing or reducing throat irritation. The methods include administering a chewing gum composition as described herein, i.e. containing an effective amount of an antitussive agent and a sufficient amount of an antitussive taste-masking mixture, to a patient requiring such treatment. The methods provide at least temporary, symptomatic relief while during the time the chewing gum composition is being chewed and thereafter due to the release of taste-masked antitussive in the oral cavity and throat areas.

A still further aspect of the invention includes a method of preparing antitussive-containing chewing gum compositions. The method includes combining a preferably softened gum base with an effective amount of an antitussive agent and antitussive taste-masking mixture containing preferably a high intensity sweetener, flavorant and menthol until a substantially homogeneous mixture is obtained and thereafter dividing the homogenous mixture into a plurality of chewing gum pieces containing an effective amount of the taste-masked antitussive agent.

As a result of the present invention there are provided chewing gum compositions containing antitussive ingredients which have an acceptable taste with minimum bitter aftertaste even after prolonged periods of chewing. The ability to provide medicated-chewing gums which can be chewed for periods in excess of 15 minutes without losing a substantial amount their flavor and delivering an antitussive is therapeutically advantageous. For example, the chewing process allows the antitussive to be released over an extended period and be combined with saliva to produce a soothing effect on the irritated throat and thus quell the coughing for longer periods.

For purposes of the present invention, the term "effective amount" shall be understood to be an amount that is sufficient to significantly effect a positive clinical response. In this case a positive clinical response includes temporary cough suppression and/or temporary relief of throat irritation.

For purposes of the present invention, the term "sufficient amount" shall be understood to mean an amount which is capable of providing the desired effect, especially in the chewing gum compositions. For example, the taste-masking mixtures described herein are included in the chewing gum compositions in amounts which are at least effective to substantially neutralize the unpleasant taste qualities associated with the medicament in the chewing gum composition during the chewing period.

The term "antitussive" for purposes of the present invention shall be understood to include all medicaments associated with not only cough suppression but also medicaments having at least a temporary palliative effect on throat irritation.

For a better understanding of the present invention, together with other and further objects, reference is made to the following description. The scope of the present invention will be pointed out in the appended claims.

DETAILED DESCRIPTION OF THE INVENTION

The present invention provides chewing gum compositions containing antitussive compounds and unpleasant taste masking mixtures which serve to improve the taste of the medicament gum by substantially masking any unpleasant taste, bitter or off-note associated with the medicament for a prolonged period of time. In one aspect, there is provided a chewing gum composition containing an effective amount of an antitussive ingredient and a sufficient amount of a taste-masking mixture of ingredients which preferably include a high intensity sweetener, a flavorant and menthol. The chewing gum compositions are capable of delivering an antitussive effect upon chewing substantially without imparting the unpleasant taste or off notes associated with such medicaments during the time the composition is being chewed.

The antitussive ingredients contemplated for inclusion in the chewing gum compositions of the present invention can be selected from the following non-limiting list:

dextromethorphan, dextromethorphan hydrobromide, noscapine, carbetapentane citrate, chlophendianol hydrochloride, menthol, opiate-based cough suppressants such as codeine, codeine phosphate, codeine sulfate, hydrocodone, hydrocodone bitartrate, morphine, morphine sulphate, beechwood creosote, benzonatate, camphor, ethanedisulfonate, combinations thereof and the like. Preferred antitussive include dextromethorphan and menthol.

The amount of antitussive medicament included in the chewing gum compositions of the present invention is generally defined as an effective amount. This amount, of course, will vary according to the particular medicament selected and the size of chewing gum dosage unit. The amount of medicament or its acid addition salt used in the present invention can also vary depending upon the therapeutic dosage recommended or permitted. In general, the amount of medicament present corresponds to the ordinary dosage required to obtain the desired result. Such dosages are known to the skilled practitioner in the medical arts. It is to be understood that the amount of antitussive included will be an amount generally regarded as safe and effective for at least temporary relief of throat irritation and/or coughing. For example, in the case of dextromethorphan, the U.S. Food and Drug Administration requires that antitussive preparations deliver a dosage of 9–15 mg of dextromethorphan hydrobromide every 4 hours for adults and every 6 to 8 hours for children. Thus, the gum compositions include enough dextromethorphan in each chewing gum stick so that about 9–15 mg of the drug which will release from the chewing gum during an average chewing period and provide about two-four hours of relief In the case of menthol, the chewing gums of the present invention are designed to release between 5 and 10 mg of menthol during an average chew period. For purposes of the present invention, average chewing periods are estimated to be about 10–20 minutes.

With the foregoing dosage guidelines in mind and assuming that the average weight of a stick of chewing gum is about 3 grams, the chewing gum compositions of the present invention contain, on a weight basis, from about 0.1 to about 1.0% antitussive, preferably from about 0.12 to about 0.75%, and most preferably from about 0.12 to about 0.75% by weight antitussive. It will be understood by those of ordinary skill that it may be necessary to include amounts of the medicament which are slightly greater than the amounts set forth above in those cases where the gum base selected is know to prevent complete release of the medicament. Such variations, if required, will be apparent and not subject to undue experimentation by those of ordinary skill.

The chewing gum compositions can also include one or more additional medicaments which act in a therapeutically complementary fashion with the antitussive compound. For example, the chewing gums can include one or more of the following compositions selected from a wide variety of drugs and their acid addition salts. Both organic and inorganic salts may be used provided the drug maintains its medicament value. Exemplary acid salts include hydrochloride, hydrobromide, orthophosphate, benzoate, maleate, tartrate, succinate, citrate, salicylate, sulfate and acetate. A non-limiting list of illustrative categories and specific examples includes:

- antihistamines, such as chlorpheniramine maleate, phenindamine tartrate, pyrilamine maleate, doxylamine succinate, phenyltoloxamine citrate, diphenhydramine hydrochloride, promethazine and triprolidine;
- decongestants, such as phenylephrine hydrochloride, phenylpropanolamine hydrochloride, pseudoephedrine hydrochloride and ephedrine;
- expectorants, such as guaifenesin;
- non-steriodal anti-inflammatory agents, such as ibuprofen, ketoprofen and naproxen;
- analgesics or antipyretics such as aspirin or acetaminophen.

Those of ordinary skill will realize that those medicaments not specifically mentioned but known to be of complementary value with antitussives are also intended for inclusion in the present invention.

In one preferred embodiment the supplemental medicament is selected from the group consisting of diphenhydramine, pseudoephedrine, pseudoephedrine hydrochloride, guaifenesin and mixtures thereof. In an alternative embodiment, the chewing gum compositions include a member of the group consisting of decongestant agents, expectorants, antihistamines and combinations thereof in addition to the antitussive.

The medicaments of the present invention can be used in many distinct physical forms well known in the pharmaceutical art to provide an initial dosage of the medicament and/or a time-release form of the medicament. Without being limited thereto, such physical forms include free forms and encapsulated forms, and mixtures thereof.

The taste-masking mixtures included in the chewing gum compositions of the present invention include a high intensity sweetener, a flavorant and menthol. The menthol included in the taste-masking mixture is an additional amount over that which can be used as a medicament discussed above. The amount of taste masking mixture employed herein is that amount sufficient to nullify the bitter taste or unpleasant off-note of the antitussive agent having a bitter or unpleasant off-note. The amount of taste-masking mixture employed in the chewing gum compositions is normally a matter of preference and is subject to such factors as the selected intense sweetener, flavoring agent and amount of menthol included as well as the degree of unpleasant off-note associated with the medicament. The amount of each portion of the mixture as represented in the total chewing gum composition however, is set forth below. Variations in the amount of each portion of the mixture in order to obtain the result desired in the final taste masking for the final product and such variations, are within the capabilities of those skilled in the art without the need for undue experimentation. In one aspect of the invention, the final chewing gum compositions include (by weight):

high intensity sweetener: about 0.0001 to about 5.0%;
flavorant: about 0.0001 to about 5.0%; and
menthol: about 0.001 to about 1.5%.

Preferably, the high intensity sweetener is present in amounts from about 0.02 to about 1.5% by weight and most preferably in amounts from about 0.05 to about 1.0% by weight.

The flavorant is preferably present in amounts from about 0.1 to about 5.0% by weight and most preferably in amounts from about 0.5 to about 3.0% by weight.

The menthol is preferably present in amounts from about 0.01 to about 1.0% by weight and most preferably in amounts from about 0.025 to about 0.4% by weight when included as part of the taste-masking mixture.

The high intensity sweetener compounds useful in the taste-masking mixture include dipeptides such as N-L-alpha-aspartyl-L-phenylalanine 1-methyl ester (Aspartame), a commercially available product of the Nutrasweet Company, Deerfield, Ill., saccharin, available from Cumberland Packing Co. of Brooklyn N.Y., proteins such as thaumatin (Talin), a commercially available product of Tate & Lyle Products, Reading, United Kingdom, dihydrochalcones, Acesulfame-K, a commercially available product of Hoechst Celanese Corporation, Somerville, N.J., Sucralose, a product of McNeil Specialty Products Company, Skillman, N.J. and Alitame, a product of Pfizer, New York, N.Y. Combinations of the foregoing can also be included in the compositions of the present invention. Preferably, the high intensity sweetener is selected from the group consisting of aspartame, saccharin, sucralose, acesulfame K, alitame and mixtures thereof. Most preferably, the high intensity sweetener is aspartame.

The intense sweetener of the present invention may be used in many distinct physical forms well known in the art to provide an initial burst of sweetness and flavor and/or a prolonged sensation of sweetness and flavor. Without being limited thereto, such physical forms include free forms, such as spray dried, powdered, and beaded forms, and encapsulated forms, and mixtures thereof.

The flavoring agents (flavors, flavorings) of the present invention include those flavors known to the skilled artisan. These flavoring agents include natural, artificial and synthetic flavor oils and flavoring aromatic and/or oils, oleoresins and extracts derived from plants, leaves, flowers, fruits, and so forth, and combinations thereof. Non-limiting representative flavor oils include spearmint oil, peppermint oil, eucalyptus oil, oil of nutmeg, allspice, mace, oil of bitter almonds, menthol and the like. Also useful flavorings are artificial, natural and synthetic fruit flavors such as citrus oils including lemon, orange, lime, grapefruit, and fruit essences including apricot and so forth. These flavoring agents may be used in liquid or solid form and may be used individually or in admixture.

Other useful flavorings include aldehydes and esters such as benzaldehyde (cherry, almond), citral, i.e., alpha-citral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), and 2-dodecenal (citrus, mandarin), mixtures thereof and the like.

In a preferred embodiment, one of the flavoring agents is honey or an artificial honey flavor. The flavoring agent may be employed in either liquid form and/or dried form. When employed in the latter form, suitable drying means such as spray drying the oil may be used. Alternatively, the flavoring agent may be absorbed onto water soluble materials, such as cellulose, starch, sugar, maltodextrin, gum arabic and so forth or may be encapsulated.

The flavoring agent of the present invention may be used in many distinct physical forms well known in the art to provide a initial burst of flavor and/or a prolonged sensation of flavor. Without being limited thereto, such physical forms include free forms, such as spray dried, powdered, and beaded forms, and encapsulated forms, and mixtures thereof.

The amount of flavoring agent employed herein is normally a matter of preference subject to the ranges set forth above and such factors as the individual flavor, the type of bulking agent or carrier employed, and the strength of flavor desired. Thus the amount of flavoring may be varied in order to obtain the result desired in the final product and such variations are within the capabilities of those skilled in the art without the need for undue experimentation.

In accordance with this invention, effective amounts of the unpleasant taste masking compositions of the present invention are admixed into the medicated chewing gum compositions. The amount of the unpleasant taste masking mixture employed is subject to such additional factors as the degree of bitter or off-note taste of the medicament and the therapeutically effective dosage level of the medicament. Thus, the amount of unpleasant taste masking composition may be varied on order to obtain the result desired in the final product and such variations are within the capabilities of those skilled in the art without the need for undue experimentation.

Secondary flavoring agents may also be used in the chewing gum formulations of this invention. Such additional flavors should be compatible with the unpleasant taste masking mixture and not adversely alter the overall sensory perception. The secondary flavoring agents useful to prepare the flavoring compositions of this invention include those flavorings known to the skilled artisan such as the flavorings mentioned above. The secondary flavoring agents of the present invention may be used in many distinct physical forms well known in the art to provide an initial burst of flavor and/or a prolonged sensation of flavor. Without being limited thereto, such physical forms include free forms, such as spray dried, powdered, and beaded forms, and encapsulated forms, and mixtures thereof. The amounts of secondary flavoring agent employed in the chewing gum composition of this invention is normally a matter of preference. In general, the secondary flavoring agent is present in amounts from about 0.02% to about 5%, by weight of the gum composition. Preferably, the secondary flavoring agent is present in amounts from about 0.1% to about 2%, by weight, and more preferably, the secondary flavoring agent is present in amounts from about 0.3% to about 1.5%, by weight of the chewing gum composition.

It has unexpectedly been found that a mixture of menthol, aspartame, or other artificial sweeteners, and honey flavor in sugarless gums provide a useful vehicle for dispensing menthol or dextromethorphan as antitussive agents without unpleasant taste notes. The resulting gum provides a sustained long lasting relief and soothing effect for periods exceeding 30 minutes. Similar results are observed in sugar-containing chewing gums. In this aspect of the invention, the artificial sweetener can be reduced or even eliminated based on the sweetener included.

Chewing gums are known to those skilled in the art to include:
a gum base component;
a water soluble sweetener component such as sucrose, sorbitol, xylitol, either alone or in combination with intense sweeteners such as saccharin or aspartame; an emulsifier such as lecithin;
a plasticizer such as corn syrup, hydrogenated corn syrup; and
flavoring agents.

The chewing gum compositions of the present invention incorporating the antitussives and unpleasant taste masking mixture can be in the form of both chewing gum and bubble gum formulations. The gum base employed will vary greatly depending upon various factors such as the type of base desired, the consistency of gum desired and the other components used in the composition to make the final chewing gum product. The gum base may be any water-insoluble gum base known in the art, and includes those gum bases utilized for chewing gums and bubble gums. Illustrative examples of suitable polymers in gum bases include both natural and synthetic elastomers and rubbers. For example, those polymers which are suitable as gum bases include, without limitation, substances of vegetable origin such as chicle, crown gum, nispero, rosadinha, jelutong, periollo, niger gutta, tunu, balata, gutta-percha, lechi-capsi, sorva, gutta kay, mixtures thereof and the like. Synthetic elastomers such as butadiene-styrene copolymers, polyisobutylene, isobutyleneisoprene copolymers, polyethylene, mixtures thereof and the like are particularly useful. The gum base may include a non-toxic vinyl polymer, such as polyvinyl alcohol, and mixtures thereof. When utilized, the molecular weight of the vinyl polymer may range from about 3,000 up to and including about 94,000. The amount of gum base employed will vary greatly depending upon various factors such as the type of base used, the consistency of the gum desired and the other components used in the composition to make the final chewing gum product. In general, the gum base will be present in amounts from about 5% to about 94%, by weight of the final chewing gum composition. Preferably, the gum base is used in amounts from about 15% to about 45%, and more preferably in amounts from about 15% to about 35% by weight of the final chewing gum composition.

The gum base composition may contain conventional elastomer solvents to aid in softening the elastomer base component. Such elastomer solvents may comprise terpinene resins such as polymers of alpha-pinene or beta-pinene, methyl, glycerol or pentaerythritol esters of rosins or modified rosins and gums, such as hydrogenated, dimerized or polymerized rosins or mixtures thereof. Examples of elastomer solvents suitable for use herein include the pentaerythritol ester of partially hydrogenated wood or gum rosin, the pentaerythritol ester of wood or gum rosin, the glycerol ester of wood rosin, the glycerol ester of partially dimerized wood or gum rosin, the glycerol ester of tall oil rosin, the glycerol rosin, the glycerol ester of tall oil rosin, the glycerol ester of wood or gum rosin and the partially hydrogenated wood or gum rosin and the partially hydrogenated methyl ester of wood or rosin, mixtures thereof, and the like. The elastomer solvent may be employed in amounts from about 5.0% to about 75.0%, by weight of the gum base, and preferably from about 45.0% to about 70.0%, by weight of the gum base.

A variety of traditional ingredients may be included in the gum base in effective amounts such as plasticizers or softeners such as lanolin, palmitic acid, oleic acid, stearic acid, sodium stearate, potassium stearate, glyceryl triacetate, glyceryl lecithin, glyceryl monostearate, propylene glycol monostearate, acetylated monoglyceride, glycerine, mixtures thereof, and the like may also be incorporated into the gum base to obtain a variety of desirable textures and consistency properties. Waxes, for example, natural and synthetic waxes, hydrogenated vegetable oils, petroleum waxes such as polyurethane waxes, polyethylene waxes, paraffin waxes, microcrystalline waxes, fatty waxes, sorbitan monostearate, tallow, propylene glycol, mixtures thereof, and the like may also be incorporated into the gum base to obtain a variety of desirable textures and consistency properties. These traditional additional materials are generally employed in amounts up to about 30.0%, by weight of the gum base, and preferably in amounts from about 3% to about 20%, by weight of the gum base.

The gum base may include effective amounts of mineral adjuvants such as calcium carbonate, magnesium carbonate, alumina, aluminum hydroxide, aluminum silicate, talc, tricalcium phosphate, dicalcium phosphate and the like as well as mixtures thereof. These mineral adjuvants may serve as fillers and textural agents. These fillers or adjuvants may be used in the gum base in various amounts. Preferably the amount of filler when used will be present in an amount from greater than about 0% to about 60%, by weight of the chewing gum base.

The chewing gum base may additionally include the conventional additives of coloring agents, antioxidants, preservatives and the like. For example, titanium dioxide and other dyes suitable for food, drug and cosmetic applications, known as F.D. & C. Dyes, may be utilized. An anti-oxidant such as butylated hydroxytoluene (BHT), butylated hydroxyanisole (BHA), propyl gallate, and mixtures thereof, may also be included. Other conventional chewing gum additives known to one having ordinary skill in the chewing gum art may also be used in the chewing gum base.

The gum composition may include effective amounts of conventional additives selected from the group consisting of sweetening agents (sweeteners), plasticizers, softeners, emulsifiers, waxes, fillers, bulking agents, mineral adjuvants, flavoring agents (flavors, flavorings), coloring agents (colorants, colorings), antioxidants, acidulants, thickeners, mixtures thereof and the like. Some of these additives may serve more than one purpose. For example, in sugarless gum compositions, the sweetener, e.g., sorbitol or other sugar alcohol or mixtures thereof, may also function as a bulking agent. Similarly, in sugar containing gum compositions, the sugar sweetener can also function as a bulking agent. The plasticizers, softeners, mineral adjuvants, colorants, waxes and antioxidants discussed above as being suitable for use in the gum base may also be used in the gum composition. Examples of other conventional additives which may be used include emulsifiers, such as lecithin and glyceryl monostearate, thickeners, used alone or in combination with other softeners, such as methylcellulose, alginates, carrageenan, xanthan gum, gelatin carob, tragacanth, locust bean, and carboxylmethylcellulose, acidulants such as malic acid, adipic acid, citric acid, tartaric acid, fumaric acid, and mixtures thereof, and fillers, such as those discussed above under the category of mineral adjuvants. The fillers when used may be utilized in an amount from greater than about 0% to about 60%, by weight of the gum composition. Bulking agents (carriers, extenders) suitable for use include sweetening agents selected from the group consisting of monosaccharides, disaccharides, polysaccharides, sugar alcohols, and mixtures thereof; polydextrose; maltodextrins; minerals, such as calcium carbonate, talc, titanium dioxide, dicalcium phosphate, and the like. Bulking agents may be used in amounts up to about 90%; by weight of the final gum composition, with amounts from about 40% to about 70%, by weight of the gum composition being preferred, with from about 50% to about 65%, by weight, being more preferred and from about 55% to about 60%, by weight of the chewing gum composition, being most preferred.

The sweetening agent used may be selected from a wide range of materials including water-soluble sweeteners, water-soluble artificial sweeteners, water-soluble sweeteners derived from naturally occurring water-soluble sweeteners, dipeptide based sweeteners, and protein based sweeteners, including mixtures thereof. Without being limited to particular sweeteners, representative categories and examples include:

(a) water-soluble sweetening agents such as monosaccharides, disaccharides and polysaccharides such as xylose, ribulose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof;

(b) water-soluble artificial sweeteners such as soluble saccharin salts, i.e., sodium or calcium saccharin salts, cyclamate salts, the sodium, ammonium or calcium salts of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like;

(c) dipeptide based sweeteners, such as L-aspartic acid derived sweeteners, such as L-aspartyl-L-phenylalanine methyl ester (Aspartame) and materials described in U.S. Pat. No. 3,492,131, L-alpha-aspartyl-N-(2,2,4,4-tetramethyl-3-thietanyl)-D-alaninamide hydrate (Alitame), methyl esters of L-aspartyl-L-phenyl-glycerine and L-aspartyl-L-2,5-dihydrophenylglycine, L-aspartyl-2,5-dihydro-L-phenylalanine; L-aspartyl-L-(1-cyclohexen)-alanine, and the like;

(d) water-soluble sweeteners derived from naturally occurring water-soluble sweeteners, such as chlorinated derivatives of ordinary sugar (sucrose), known, for example, under the product designation of Sucralose; and (e) protein based sweeteners such as thaumaoccous danielli (Thaumatin I and II).

In general, an effective amount of sweetener is utilized to provide the level of bulk and/or sweetness desired, and this amount will vary with the sweetener selected. This amount of sweetener will normally be present in amounts from about 0.0025% to about 90%, by weight of the gum composition, depending upon the sweetener used. The exact range of amounts for each type of sweetener is well known in the art and is not the subject of the present invention. The amount of sweetener ordinarily necessary to achieve the desired level of sweetness is independent from the flavor level achieved from flavor oils. Preferred sugar based-sweeteners are sugar (sucrose), corn syrup and mixtures thereof. Preferred sugarless sweeteners are the sugar alcohols, artificial sweeteners, dipeptide based sweeteners and mixtures thereof. Preferably, sugar alcohols are used in the sugarless compositions because these sweeteners can be used in amounts which are sufficient to provide bulk as well as the desired level of sweetness. Preferred sugar alcohols are selected from the group consisting of sorbitol, xylitol, maltitol, mannitol, and mixtures thereof. More preferably, sorbitol or a mixture of sorbitol and mannitol is utilized. The gamma form of sorbitol is preferred. An artificial sweetener or dipeptide based sweetener is preferably added to the gum compositions which contain sugar alcohols.

The coloring agents useful in the present invention are used in amounts effective to produce the desired color. These coloring agents include pigments which may be incorporated in amounts up to about 6%, by weight of the gum composition. A preferred pigment, titanium dioxide, may be incorporated in amounts up to about 2%, and preferably less than about 1%, by weight of the composition. The colorants may also include natural food colors and dyes suitable for food, drug and cosmetic applications. These colorants are known as F.D. & C. dyes and lakes. The materials acceptable for the foregoing uses are preferably water-soluble. Illustrative non-limiting examples include the indigoid dye known as F.D. & C. Blue No. 2, which is the disodium salt of 5,5-indigotindisulfonic acid. Similarly, the dye known as F.D. & C. Green No. 1 comprises a triphenyl-methane dye and is the monosodium salt of 4-[4-(N-ethyl-p-sulfoniumbenzylamino) diphenylmethylene]-[1-(N-ethyl-N-p-sulfoniumbenzyl)-delta-2,5-cyclohexadieneimine]. A full recitation of all F.D. & C. colorants and their corresponding chemical structures may be found in the Kirk Othmer Encyclopedia of Chemical Technology, 3rd Edition, in volume 5 at pages 857–884, which text is incorporated herein by reference.

Another aspect of the present invention provides methods of treatment for various medical conditions associated with coughing and/or throat irritation. The methods include administering an effective amount of the chewing gum compositions described herein to a patient in need of such treatment. The medicated chewing gum compositions are useful for, among other things, treating cough and/or throat irritations associated with colds, allergies, and related conditions which would respond positively or favorably as these terms are known in the medical arts to antitussive-based therapy.

The amount of chewing gum composition administered to the patient in need thereof in order to treat the conditions described above is based on the amount of medicament (i.e. antitussive) included in the chewing gum composition. For example, it is contemplated that a suitable chewing gum dosage form would be about 3 grams and contain from about 9 milligrams to about 15 milligrams of deliverable dextromethorphan hdyrobromide. Such dosage forms could be administered every 2 to 4 hours for adults and/or every 6 to 8 hours for children.

Naturally, the doses of the various antitussive medicaments included in the chewing gum compositions of the present invention will vary somewhat depending upon the medicament and chewing gum ingredients selected. It is contemplated, however, that the range of medicaments set forth above is illustrative of suitable doses and those skilled in the art will determine optimal dosing of the medicament containing chewing gum compositions based on clinical experience and the treatment indications.

The present invention also includes a method of preparing the medicament-containing chewing gum compositions described above.

Each of the resultant pieces will contain an effective amount of an antitussive agent and a sufficient amount of said antitussive taste-masking mixture to mask the taste of the antitussive agent for the time the chewing gum piece is being chewed.

The methods thus generally include admixing the medicament unpleasant taste masking mixture components with the other ingredients of the final desired ingredients of the final chewing gum.

Other ingredients will usually be incorporated into the composition as dictated by the nature of the desired composition as well known to those of ordinary skill in the art. The ultimate ingestible compositions are readily prepared using methods generally known in the food technology and pharmaceutical arts.

The medicament and unpleasant taste masking mixture can be incorporated into an otherwise conventional chewing gum composition using conventional techniques and equipment known to those skilled in the art. For example, a gum base is heated to a temperature sufficiently high enough to soften the base without adversely effecting the physical and chemical make up of the base. The optimum temperatures utilized may vary depending upon the composition of the gum base used, but such temperatures are readily determined by those skilled in the art without undue experimentation. The gum base is conventionally melted at temperatures that range from about 60° C. to about 120° C. For a period of time sufficient to render the base molten. For example, the gum base may be heated under these conditions for a period of about thirty minutes just prior to being admixed incrementally with the remaining ingredients of the base such as the plasticizer, fillers, the bulking agent and/or sweeteners, the softener and coloring agents to plasticize the blend as well as to modulate the hardness, viscoelasticity and formability of the base. The chewing gum base is then blended with the flavoring agents high intensity sweetener, medicament and, optionally other traditional ingredients. Mixing is continued until a uniform mixture of gum composition is obtained. Thereafter the gum composition mixture may be formed into desirable chewing gum shapes.

EXAMPLES

The following examples serve to provide further appreciation of the invention but are not meant in any way to restrict the effective scope of the invention.

Example 1

A control sugarless chewing gum was prepared in accordance with the following formulation and procedure:

Control Gum

| Ingredient | Percent |
| --- | --- |
| Sorbitol powder | 58.95 |
| Gum base | 20.00 |
| Lycasin | 17.20 |
| Honey flavor | 1.50 |
| Peppermint oil | 1.00 |
| Spray dried peppermint flavor | 0.50 |
| Lecithin | 0.50 |
| Aspartame (APM) | 0.35 |
| | 100.00 |

The gum base was melted in a sigma blade mixer and then cooled to 180° F. Lecithin was added and mixed for 2 minutes. Oil and flavor were added and mixed for 2 minutes. One half of the APM together with one half of the sorbitol were added and mixed for 2 minutes. Lycasin and remainder of sorbitol were added and mixed for 5 minutes. Spray dried flavor and the remainder of APM were added and mixed until a uniform mixture was formed. The bulk composition was rolled and scored into 3 gram sticks.

This control gum was evaluated by several judges and was found to have an excellent flavor. However, the judges felt that the product lost its flavor after about 7 minutes of chewing.

Example 2

Menthol Gum

| Ingredient | Percent |
|---|---|
| Sorbitol powder | 58.95 |
| Gum base | 20.00 |
| Lycasin | 17.00 |
| Liquid Honey flavor | 1.50 |
| Peppermint oil | 1.00 |
| S.D. Peppermint oil | 0.50 |
| Yelkin | 0.50 |
| APM | 0.35 |
| Menthol crystals | 0.20 |
| | 100.00 |

Chewing gums containing menthol were prepared as described in Example 1. The only difference in the formulation was that the Lycasin content was reduced to 17.0% and 0.20% menthol crystals were added. Thus, the amount of menthol in a 3 gram stick is 6 milligrams. Half of the menthol was added together with the first half of APM. The other half was added together with the sorbitol powder.

This chewing gum was evaluated in the same manner as the control gum. Surprisingly, the gum had considerable flavor even after 30 minutes of chewing. Judges described the gum as soothing and causing salivation which was expected from an antitussive-containing gum.

Example 3

The menthol content was increased to 0.3% from 0.2% (Example 2), thus delivering 9 mg. of menthol per 3 g. stick. The product was highly acceptable and similar to the product of Example 2.

Example 4

The gum described in Example 3 was prepared except that most of the menthol was replaced with dextromethorphan at 0.3%. A small amount, 0.05% of the menthol, was kept in the gum to provide longer lasting flavor and provide the composition with a complete taste-masking mixture. The gum was evaluated by judges who found the product highly acceptable. The flavor of this gum lasted for over 30 minutes. The bitter taste associated with dextromethorphan was not detected during the chew period.

Example 5

Sugar Sweetened Menthol Gum

| Ingredient | Percent |
|---|---|
| Powdered sugar | 60.7 |
| Gum base | 20.0 |
| Honey | 17.0 |
| Peppermint Oil | 1.0 |
| Menthol Crystals | 0.2 |
| APM | 0.1 |
| Liquid honey flavor | 0.5 |
| S.D. peppermint oil | 0.5 |
| | 100.0 |

In this Example, a sugar sweetened menthol gum was prepared in accordance with the present invention. The gum base heated and then cooled to about 180°. The oil flavor, menthol crystals and APM were then added and the combination was mixed for two minutes. The sugar and honey were then added alternatively and mixing was continued for an additional two minutes. Next, the honey flavor was added and the mixing was continued a still further two minutes. Finally, the spray dried flavor was added and the combination was mixed a final two minutes. The resultant product was rolled and scored into chewing gum sticks weighing about 3 grams.

This chewing gum was evaluated by judges and compared to a control gum prepared in the same manner as above except that no menthol was included. The inventive gum was determined to have considerable flavor even after 30 minutes of chewing. The judges described the gum as soothing to the throat and causing salivation.

While there have been described what is presently believed to be to the preferred embodiments of the invention, those skilled in the art will realize that changes and modifications may be made thereto without departing from the spirit of the invention and it is intended to claim all such changes and modifications that fall within the true scope of the invention.

What is claimed is:

1. A chewing gum composition capable of delivering an antitussive upon chewing comprising
   an effective amount of an antitussive agent and
   a sufficient amount of an antitussive taste-masking mixture, said taste-masking mixture consisting essentially of a high intensity sweetener, a flavorant and menthol; said taste-masking mixture masking the taste of said antitussive agent during the time said chewing gum composition is being chewed.

2. The chewing gum composition of claim 1, wherein said antitussive is selected from the group consisting of dextromethorphan, dextromethorphan hydrobromide, noscapine, carbetapentane citrate, chlophendianol hydrochloride, menthol, codeine, codeine phosphate, codeine sulfate, diphenhydramine, diphenhydramine hydrochloride, hydrocodone, hydrocodone bitartrate, morphine, morphine sulphate, opiate-based cough suppressants, beechwood creosote, benzonatate, camphor, ethanedisulfonate and combinations thereof.

3. The chewing gum composition of claim 2, wherein said antitussive is dextromethorphan.

4. The chewing gum composition of claim 1, wherein said antitussive agent is present in an amount of from about 0.01 to about 2.5% by weight.

5. The chewing gum composition of claim 4, wherein said antitussive agent is present in an amount of from about 0.1 to about 1.0% by weight.

6. The chewing gum composition of claim 5, wherein said antitussive agent is present in an amount of from about 0.1 2 to about 0.75% by weight.

7. The chewing gum composition of claim 1, wherein said chewing gum composition comprises by weight about 0.0001 to about 5.0% high intensity sweetener; about 0.0001 to about 5.0% flavorant; and about 0.001 to about 1.5% menthol.

8. The chewing gum composition of claim 1, wherein said high intensity sweetener is selected from the group consisting of aspartame, saccharin, sucralose, alitame, acesulfame K and mixtures thereof.

9. The chewing gum composition of claim 8, wherein said high intensity sweetener is aspartame.

10. The chewing gum composition of claim 1, wherein said high intensity sweetener is present in an amount of from about 0.02 to about 1.5% by weight.

11. The chewing gum composition of claim 10, wherein said high intensity sweetener is present in an amount of from about 0.05 to about 1.0% by weight.

12. The chewing gum composition of claim 1, wherein said flavorant comprises honey or an artificial honey flavor.

13. The chewing gum composition of claim 1, wherein said flavorant is present in an amount of from about 0.1 to about 5.0% by weight.

14. The chewing gum composition of claim 13, wherein said flavorant is present in an amount of from about 0.5 to about 3.0% by weight.

15. The chewing gum composition of claim 1, wherein said menthol of said antitussive taste-masking mixture is present in an amount of from about 0.01 to about 1.0% by weight.

16. The chewing gum composition of claim 13, wherein said menthol of said antitussive taste-masking mixture is present in an amount of from about 0.025 to about 0.1% by weight.

17. A method of effecting cough suppression in a patient requiring such treatment, comprising administering a chewing gum composition of claim 1.

18. A method of treating throat irritation in a patient requiring such treatment, comprising administering a chewing gum composition of claim 1.

19. The chewing gum composition of claim 1, wherein the flavorant is a flavorant other than menthol such that the amount of menthol in said antitussive taste-masking mixture is additional to the amount of the flavoring.

20. A method of preparing a chewing gum composition capable of delivering an antitussive upon chewing comprising the steps of:

a) obtaining an antitussive agent;

b) forming an antitussive taste-masking mixture consisting essentially of a high intensity sweetener, a flavorant and menthol, said antitussive taste-masking mixture being of an amount sufficient to mask the taste of the antitussive agent;

c) mixing the antitussive agent and the taste-masking mixture with a gum base until a substantially homogeneous mixture is obtained with the antitussive agent and until the taste-masking mixture is distributed throughout the homogeneous mixture; and d) dividing said homogeneous mixture into a plurality of chewing gum pieces, whereby each of said chewing gum pieces contains an effective amount of said antitussive agent and a sufficient amount of said antitussive taste-masking mixture to mask the taste of said antitussive agent for the time said chewing gum piece is being chewed.

21. A chewing gum composition capable of delivering an antitussive upon chewing while masking an unpleasant taste of the antitussive, consisting essentially of:

an effective amount of an antitussive agent and a sufficient amount of an antitussive taste-masking mixture, said taste-masking mixture consisting of a high intensity sweetener, a flavorant and menthol; said taste-masking mixture masking the taste of said antitussive agent during the time said chewing gum composition is being chewed.

* * * * *